United States Patent [19]

Naylor

[11] Patent Number: 4,704,226

[45] Date of Patent: Nov. 3, 1987

[54] PROCESS FOR THICKENING AQUEOUS SOLUTIONS

[75] Inventor: Carter G. Naylor, Austin, Tex.

[73] Assignee: Texaco, Inc., White Plains, N.Y.

[21] Appl. No.: 798,095

[22] Filed: Nov. 14, 1985

[51] Int. Cl.$^4$ .............................................. C09D 9/00
[52] U.S. Cl. ..................................... 252/162; 424/70; 514/844
[58] Field of Search ......................... 252/162; 424/70; 514/844

[56] References Cited

U.S. PATENT DOCUMENTS

| | | | |
|---|---|---|---|
| 2,047,069 | 7/1936 | Hentrich et al. | 252/173 X |
| 2,674,580 | 4/1954 | Henkin | 252/548 X |
| 3,954,660 | 5/1976 | Kennedy et al. | 252/353 |
| 3,962,418 | 6/1976 | Birkofer | 424/70 |
| 4,261,851 | 4/1981 | Duke | 252/174.21 |
| 4,375,421 | 3/1983 | Rubin et al. | 252/110 |
| 4,404,109 | 9/1983 | Tellier et al. | 252/8.55 |
| 4,490,355 | 12/1984 | Desai | 424/70 |

FOREIGN PATENT DOCUMENTS

| | | | |
|---|---|---|---|
| 0132961A1 | 2/1985 | European Pat. Off. | 252/353 |
| 0133345A1 | 2/1985 | European Pat. Off. | 252/353 |
| 2047129 | 3/1972 | Fed. Rep. of Germany | 424/61 |
| 1431698 | 2/1966 | France | 424/65 |
| 46-14357 | 4/1971 | Japan | 424/65 |
| 50-75576 | 6/1975 | Japan | 514/554 |
| 2143841A | 2/1985 | United Kingdom | 252/353 |

OTHER PUBLICATIONS

"Surfactants in Cosmetics," vol. 16, Surfactant Science Series, M. M. Rieger, ed., Marcel Dekker (1985), Chapter 9, pp. 251–292.

B. R. Donaldson and E. T. Messenger, Int. J. Cosmetic Science, 1, 71–90 (1979).

G. Felletschin, Tenside Detergents, 1, 16–18 (1970).

*Primary Examiner*—Dale R. Ore
*Attorney, Agent, or Firm*—Jack H. Park; Kenneth R. Priem; Cynthia L. Kendrick

[57] ABSTRACT

The viscosity of cosmetic cleansing composition is increased by admixing with such compositions an effective amount of a thickener comprising an alpha-acetamido-fatty acid soap.

9 Claims, No Drawings

PROCESS FOR THICKENING AQUEOUS SOLUTIONS

BACKGROUND OF THE INVENTION

1. Field of the Invention

This invention concerns the field of thickeners for cosmetic cleansing agents.

2. Description of the Related Art

Because cosmetic cleansing agents are often applied to vertical or otherwise non-level surfaces, it is considered advantageous for the formulation to have an increased viscosity so as to inhibit the propensity of the composition to flow. There are a variety of methods known to thicken compositions containing anionic surfactants. See *Surfactants In Cosmetics,* Vol. 16 of Surfactant Science Series, M. M. Rieger, Ed., Marcel Dekker 1985, Chap. 9, pp. 251-292, for a discussion of related topics.

U.S. Pat. No. 3,954,660 to Kennedy, et al. proposes increasing the viscosity of anionic surfactant slurries by admixing with such slurries an effective amount of an additive selected from the group consisting of dialkyl ethers, alkoxyethoxyethanols and tertiary amines having the general formula $R_3N$, wherein R is an alkyl group containing from 2 to 4 carbon atoms.

Polymeric thickeners are known to capitalize on the hydration and swelling properties of high molecular weight polymers and the chain extension and hydrogen-bonding of polymer units to achieve an increase in viscosity. European Pat. Nos. 132,961 and 133,345 disclose liquid soap compositions containing a water-soluble polymer selected from the group consisting of hydroxyethyl cellulose and hydroxypropyl guar. A quaternary nitrogen-containing cellulose ether thickening agent is disclosed as useful in the production of mild thickened liquid shampoo compositions in U.S. Pat. No. 3,962,418 to Birkofer.

Electrolytes such as sodium and ammonium chloride, by increasing the size of the surfactant micelles, are known to raise the viscosity of surfactant formulations. Long-chain lipophiles having a hydrophilic end-group such as alkanolamides, betaines and amine oxides are also known to increase viscosity by enlarging micelles. U.S. Pat. No. 4,375,421 to Rubin, et al. discloses solutions containing alkylamido betaines and certain water-soluble inorganic and organic salts. These salts have a viscosity-building effect on aqueous compositions containing alkylamido betaines in the presence of anionic surfactants. U.S. Pat. No. 4,490,355 to Desai teaches that a mixture of cocoamidopropyl betaine and oleamidopropyl betaine improves the thickening and foam boosting properties in hair and skin care formulations.

The viscosity enhancing effect of different amides on a 15% active monoethanolamine-lauryl sufate and a 15% active sodium laureth-2 sulfate has been reported. B. R. Donaldson and E. T. Messenger, Int. J. Cosm. Sci. 1:71-90 (1979). In a different report, cocamide MEA was found to be an effective thickener. G. Felletschin, Tensile Detergents 7:16-18 (1970). Further, U.K. Patent Application No. GB 2 143 841A discloses the use of a variety of thickeners, including long-chain ($C_{12}-C_{18}$) fatty acid amides, as useful in thickened aqueous surfactant compositions.

It has also been proposed to thicken shampoos by combining two surfactants, one being a nonionic surfactant typified by dibasic and tribasic acid reaction products of alkoxylated polyol fatty esters and another being of a different type such as an amphoteric/anionic surfactant. U.S. Pat. No. 4,261,851 to Duke reports that the nonionic surfactant has a thickening effect on the composition.

Applicant has discovered that alpha-acetamido-fatty acid soaps having the general formula:

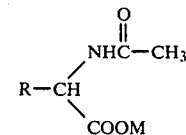

wherein R is a hydrocarbon group containing from 10-20 carbon atoms and M is a cation, display much greater thickening power than the thickeners of the prior art. These thickeners have been found to raise the viscosity of anionic surfactant formulations by increasing the size of the surfactants micelles. U.S. Pat. No. 4,404,109 to Tellier, et al. discloses a surfactant having the formula:

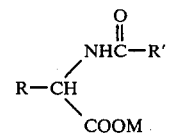

wherein R and R' are hydrocarbon groups and M is an alkali metal cation, as useful for the production of micro-emulsions in the presence of aqueous saline solutions in the assisted recovery of crude oil. Tellier, et al. describes a process that prepares a micro-emulsion of hydrocarbon and water containing a surfactant having the formula described above and a "cosurfactant," defined in the specification, examples and claims as a primary alcohol. Although it is stated that other surface-active co-agents may be used, no definition other than "the various alcohols" is provided.

SUMMARY OF THE INVENTION

The invention is a process for thickening an aqueous solution containing an anionic surfactant selected from the group consisting of alkyl sulfates, alkyl ether sulfates, alkyl benzene sulfonates and olefin sulfonates comprising the addition to the solution of an alpha-acetamido-fatty acid soap having the general formula:

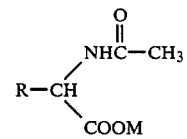

wherein R is a hydrocarbon group containing from 10-20 carbon atoms and M is a cation.

DESCRIPTION OF THE PREFERRED EMBODIMENTS

Alpha-acetamido-fatty acid soaps are found to be effective thickeners for anionic surfactants in aqueous solution. The thickened blends are suitable for hair and body shampoos, pet shampoos, skin cleansers and light duty detergents. The amido acid soaps of this invention display superiority over thickening agents most commonly used in such compositions, giving blends with much higher viscosities.

The alpha-acetamido-fatty acid soaps used to thicken these compositions have the following general formula:

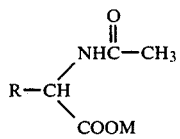

wherein R is a hydrocarbon group containing from 10–20 carbon atoms, preferably from 10–14 carbon atoms, and M is a cation, preferably selected from the group consisting of sodium, potassium, magnesium, calcium, ammonium, ethanolammonium and propanolammonium cations. It is especially preferred that M is a sodium cation. It is also preferred that the amount of the alpha-acetamido-fatty acid soap present in the composition is from about 1 to about 25 wt. % of the total active ingredients. It is especially preferred that the amount of alpha-acetamido-fatty acid soap present is from about 0.5 to about 5 wt. % of the thickened composition.

The alpha-acetamido-fatty acid soaps are prepared by neutralizing or partly neutralizing the respective amido acids with bases such as NaOH, KOH, Mg(OH)$_2$, Ca(OH)$_2$·NH$_3$, an ethanolamine or propanolamine. The amido acids may be produced from alpha olefins by carbonylation in the presence of acetamide and excess CO. The carbonylation of olefinically unsaturated compounds by reacting the olefins with carbon monoxide and a hydroxylic compound at an elevated temperature and pressure in the presence of certain metal-containing catalysts to produce carboxylic acids and derivatives of carboxylic acids is well known in the art. See, for example, U.S. Pat. Nos. 3,887,595; 4,245,115 and 4,258,206.

The concentrations of the other principal ingredients of this invention may vary. The concentration of the anionic surfactant is preferably from about 5 to about 50 wt. % of the thickened composition. Suitable anionic surfactants include alkyl sulfates, alkyl ether sulfates, alkyl benzene sulfonates and olefin sulfonates. It is preferred that the anionic surfactant is an alpha olefin sulfonate containing from 10 to 16 carbon atoms, or a mixture thereof. Further, a portion of the anionic surfactant may be replaced with a combination of anionic, amphoteric and nonionic surfactants. Water is typically the vehicle for liquid based soaps and preferably is present up to about 90 wt. %. Further, it is preferable that an inorganic salt (sodium chloride is especially preferred) be present, up to about 5 wt. %, to aid thickening.

In addition to the components mentioned, the composition may also contain conventional additives such as lathering agents, opacifying agents, conditioning agents, chelating agents, stabilizers, preservatives, colorants, fragrances and others known in the art.

The following non-limiting examples illustrate the utility of the thickeners of this invention and offer comparative data on three currently used thickeners.

EXAMPLE 1

| Sample No. | Wt. % AOS[1] | Additive | Wt. % | Visc., cs |
|---|---|---|---|---|
| A | 12.0 | $C_{10}H_{21}CH(NHCOCH_3)(CO_2Na)$ | 3.0 | 326 |
| B | 12.0 | $C_{12}H_{25}CH(NHCOCH_3)(CO_2Na)$ | 3.0 | 765 |
| C | 12.0 | $C_{14}H_{29}CH(NHCOCH_3)(CO_2Na)$ | 3.0 | 246 |
| D | 15.0 | — | — | 1.9 |
| E | 12.0 | Cocamide DEA (WITCAMIDE ® 82[2]) | 3.0 | 6.9 |
| F | 12.0 | Cocamidopropyl Betaine (TEGOBETAINE ® L-7[3]) | 3.0 | 5.6 |
| G | 12.0 | Lauramine oxide (JORDAMOX LDA[4]) | 3.0 | 21.2 |

[1]WITCONATE ® AOS is a product of Witco Chemical Co.
[2]WITCAMIDE ® 82 is a product of Witco Chemical Co.
[3]TEGOBETAINE ® L-7 is a product of Goldschmidt Chemical Co.
[4]JORDAMOX ® LDA is a product of Jordan Chemical Co.

Alpha-olefin sulfonate (AOS) alone has a very low viscosity. Three widely used surfactants, an amide, a betaine and an amine oxide, thicken the AOS only slightly. The amido acid soaps display much greater thickening power.

EXAMPLE 2

The procedures of Example 1 were followed using a cocoalkyl ether sulfate (WITCOLATE ® SE-5[1]) in place of alpha-olefin sulfonate.

| Sample No. | Wt. % Ether Sulfate | Additive | Wt. % | Visc., cs |
|---|---|---|---|---|
| H | 15.0 | — | — | 6.1 |
| I | 13.5 | $C_{10}CH(NHCOCH_3)(CO_2Na)$ | 1.5 | 59.6 |
| J | 13.5 | $C_{12}CH(NHCOCH_3)(CO_2Na)$ | 1.5 | 140 |
| K | 13.5 | $C_{14}CH(NHCOCH_3)(CO_2Na)$ | 1.5 | 84 |
| L | 13.5 | Cocamide DEA (WITCAMIDE 82) | 1.5 | 18.3 |
| M | 13.5 | Cocamidopropyl Betaine (TEGOBETAINE L-7) | 1.5 | 17.8 |
| N | 13.5 | Lauramine oxide (JORDAMOX LDA) | 1.5 | 20.6 |

[1]WITCOLATE ® SE-5 is a product of Witco Chemical Co.

Again, the amido acid soaps display viscosity boosting ability superior to that of the reference surfactants.

I claim:

1. A process for thickening an aqueous solution containing
    from about 5 to 50 wt. % an anionic surfactant selected from the group consisting of alkyl sulfates, alkyl ether sulfates, alkyl benzene sulfonates and olefin sulfonates wherein the alkyl groups contain 10–16 carbons;
    up to about 5 wt. % an inorganic salt, comprising sodium chloride;
    and up to about 90% water,
    comprising the addition of from about 1 to about 25 wt. % to the solution of an alpha-acetamido-fatty acid soap having the general formula:

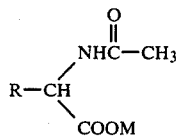

wherein R is a hydrocarbon group containing from 10–20 carbon atoms and M is a cation.

2. The process of claim 1 in which R is a hydrocarbon group containing from 10–14 carbon atoms.

3. The process of claim 1 in which M is a cation selected from the group consisting of sodium, potassium, magnesium, calcium, ammonium, ethanolammonium and propanolammonium cations.

4. The process of claim 1 in which M is a sodium cation.

5. A process for thickening an aqueous solution containing from about 5 to 50 wt. % an anionic surfactant selected from the group consisting of alkyl sulfates, alkyl ether sulfates, alkyl benzene sulfonates and olefin sulfonates wherein the alkyl groups contain 10–16 carbons;
    up to about 5 wt. % an inorganic salt, comprising sodium chloride;
    and up to about 90% water,
    comprising the addition of from about 1 to about 25 wt. % to the solution of an alpha-acetamido-fatty acid soap having the general formula:

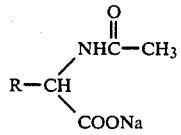

in which R is a hydrocarbon group containing from 10–14 carbon atoms.

6. A thickened composition comprising:
    (a) from about 5 to about 50 wt. % an anionic surfactant selected from the group consisting of alkyl sulfates, alkyl ether sulfates, alkyl benzene sulfonates and olefin sulfonates;
    (b) up to about 5 wt. % an inorganic salt;
    (c) up to about 90 wt. % water; and
    (d) as an essential ingredient, from about 1 to about 25 wt. % of the total active ingredients an alpha-acetamido-fatty acid soap having the general formula:

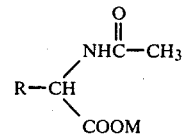

wherein R is a hydrocarbon group containing from 10–20 carbon atoms and M is a cation.

7. The thickened composition of claim 6 in which the alpha-acetamido-fatty acid soap has the formula:

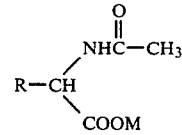

wherein R is a hydrocarbon group containing from 10–14 carbon atoms and M is a cation selected from the group consisting of sodium, potassium, magnesium, calcium, ammonium, ethanolammonium and propanolammonium cations.

8. The thickened composition of claim 6 in which the amount of alpha-acetamido-fatty acid soap present is from about 0.5 to about 5 wt. % of the thickened composition.

9. The thickened composition of claim 6 in which the alpha-acetamido-fatty acid soap has the formula:

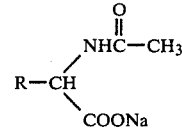

wherein R is a hydrocarbon group containing from 10–14 carbon atoms.

* * * * *